(12) United States Patent
Chiu et al.

(10) Patent No.: US 10,998,094 B1
(45) Date of Patent: May 4, 2021

(54) SYSTEMS AND METHODS FOR ALLOCATING MEDICATION IN A HIGH-VOLUME PHARMACY DISPENSING SYSTEM

(71) Applicant: Express Scripts Strategic Development, Inc., St. Louis, MO (US)

(72) Inventors: Roger Yu-Wei Chiu, Chesterfield, MO (US); Henna R. Griego, Phoenix, AZ (US); Ryan J. Phillips, University City, MO (US); Ryan Stoll, Ballwin, MO (US); Yigong Zhang, St. Louis, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 191 days.

(21) Appl. No.: 16/406,399

(22) Filed: May 8, 2019

Related U.S. Application Data

(60) Provisional application No. 62/668,495, filed on May 8, 2018.

(51) Int. Cl.
*G16H 20/13* (2018.01)
*G07F 17/00* (2006.01)
(Continued)

(52) U.S. Cl.
CPC ......... *G16H 20/13* (2018.01); *G07F 17/0092* (2013.01); *A61J 7/0084* (2013.01);
(Continued)

(58) Field of Classification Search
CPC ........ G16H 20/13; G16H 10/60; G16H 40/20; G07F 17/0092; A61J 2205/30; A61J 2205/60; A61J 7/0084
See application file for complete search history.

(56) References Cited

U.S. PATENT DOCUMENTS

| | | | | |
|---|---|---|---|---|
| 4,847,764 A | * | 7/1989 | Halvorson | ........... G06Q 10/087 |
| | | | | 700/231 |
| 5,597,995 A | * | 1/1997 | Williams | ............... G16H 20/13 |
| | | | | 235/375 |

(Continued)

OTHER PUBLICATIONS

Lu, et al., "Simplified gating in long short-term memory (lstm) recurrent neural networks." 2017 IEEE 60th International Midwest Symposium on Circuits and Systems (MWSCAS). IEEE, 2017.

(Continued)

*Primary Examiner* — Michael Collins
(74) *Attorney, Agent, or Firm* — Small Patent Law Group LLC

(57) ABSTRACT

A method includes identifying drugs to be dispensed from medication containers within filling cabinets in a pharmacy dispensing system. The drugs are automatically dispensed from the medication containers into pill containers. The method also includes determining a distribution parameter for the medication containers. The distribution parameter represents one or more of a quantity of the drugs that is dispensed or a limit on dispensing the drugs. The method also includes determining at least one allocation of the drugs in the medication containers that differs from a current allocation of the drugs in the medication containers, and changing the current allocation of the drugs in the medication containers to increase a distribution velocity at which the drugs are dispensed from the pharmacy dispensing system.

20 Claims, 10 Drawing Sheets

(51) Int. Cl.
*G16H 10/60* (2018.01)
*G16H 40/20* (2018.01)
*A61J 7/00* (2006.01)

(52) U.S. Cl.
CPC ........ *A61J 2205/30* (2013.01); *A61J 2205/60* (2013.01); *G16H 10/60* (2018.01); *G16H 40/20* (2018.01)

(56) References Cited

U.S. PATENT DOCUMENTS

| | | | |
|---|---|---|---|
| 5,720,154 | A | 2/1998 | Lasher et al. |
| 5,771,657 | A | 6/1998 | Lasher et al. |
| 5,892,512 | A | 4/1999 | Donnelly et al. |
| 7,765,776 | B1 | 8/2010 | Leu et al. |
| 9,242,751 | B1 | 1/2016 | Joplin et al. |
| 9,697,335 | B2 | 7/2017 | Joplin |
| 2004/0172162 | A1* | 9/2004 | Bonney ............. A61M 15/0043 700/237 |
| 2005/0113968 | A1* | 5/2005 | Williams ............ G07F 17/0092 700/236 |
| 2008/0319790 | A1* | 12/2008 | Vahlberg ................ G16H 40/67 705/2 |
| 2011/0313567 | A1* | 12/2011 | Willemse ............. G07F 11/165 700/242 |
| 2015/0073829 | A1* | 3/2015 | Newman ................ G16H 10/60 705/3 |
| 2015/0134360 | A1* | 5/2015 | Patrick .................. G16H 20/13 705/3 |
| 2015/0190312 | A1* | 7/2015 | Yuyama .................... A61J 7/02 700/232 |
| 2018/0122177 | A1* | 5/2018 | Este ........................ G07F 11/64 |

OTHER PUBLICATIONS https://en.wikipedia.org/wiki/Long_short-term_memory, as early as May 8, 2019.
https://en.wikipedia.org/wiki/Bin_packing_problem https://developers.google.com/optimization/bin/knapsack, as early as May 8, 2019.
https://developers.google.com/optimization/bin/knapsack, as early as May 8, 2019.

* cited by examiner

SYSTEMS AND METHODS FOR ALLOCATING MEDICATION IN A HIGH-VOLUME PHARMACY DISPENSING SYSTEM

CROSS-REFERENCE TO RELATED APPLICATIONS

This application claims priority to U.S. Provisional Application No. 62/668,495, which was filed on 8 May 2018, and the entire disclosure of which is incorporated herein by reference.

FIELD

The present application relates generally to the technical field of automated filling centers. In a specific example, the present application may relate to a high-volume fulfillment center, e.g., a high-volume pharmacy and to systems and devices used in filling prescriptions and prescription orders at a high-volume pharmacy.

BACKGROUND

A high-volume pharmacy may process and fill many prescriptions and prescription orders. Automated systems may be used by a high-volume pharmacy to process and fulfill prescriptions. Frequently, more than one prescription drug is required to complete a prescription order. Portions of the prescription order may be fulfilled in different areas of the high-volume pharmacy. After fulfillment, the fulfilled prescriptions may be gathered into a complete prescription order for shipping Some automated systems have several medication containers of different medications in different groups. Appropriate medications from these medication containers are automatically dispensed from the medication containers in the groups into prescription bottles when the prescription bottles are disposed beneath a group of medication containers having the medication to be dispensed. As medications are distributed from the medication containers, one or more medication containers may run out of the units of medication held in the medication container(s). This can prevent the group of medication containers from further distribution of the depleted medication until the medication container(s) are replenished with the medication. The time needed to replenish the medication in the depleted medication container(s) can slow down the speed at which units of medication are dispensed from the medication containers in the group that includes the depleted medication container(s). As a result, throughput of prescription orders through the high-volume pharmacy may be slowed or reduced.

The accuracy and efficiency in which these systems distribute medications can be important for the pharmacies. But, given the wide variety of medications, the changing demands for different medications, the changing supplies of medications, and the like, identifying more efficient ways to locate the medications within the systems can present difficult problems. Pharmacies may be more concerned with simply distributing medications rather than determining a more efficient arrangement of the medication containers, which can result in increased efficiency and accuracy in dispensing the medications.

BRIEF SUMMARY

In one embodiment, a method includes identifying medications to be dispensed from medication containers within filling cabinets in a pharmacy dispensing system. The medications are automatically dispensed from the medication containers into consumer pill containers. A pill container includes an enclosed body in which a consumable product can be stored. Examples of a pill container include a pill bottle, pill package, etc. The method also includes determining a distribution parameter for the medication containers. The distribution parameter represents a quantity of the medications that is dispensed and/or a limit on dispensing the medications. The method also includes determining at least one allocation of the medications in the medication containers that differs from a current allocation of the medications in the medication containers, and changing the current allocation of the medications in the medication containers to increase a distribution velocity at which the medications is dispensed from the pharmacy dispensing system.

In one embodiment, a tangible and non-transitory computer readable medium is provided. The medium includes instructions that direct one or more processors to identify medications to be dispensed from medication containers within filling cabinets in a pharmacy dispensing system. The medications are automatically dispensed from the medication containers into pill containers. The instructions also direct the one or more processors to determine a distribution parameter for the medication containers. The distribution parameter represents a quantity of the medications that is dispensed and/or a limit on dispensing the medications. The instructions also direct the processors to determine an allocation of the medications in the medication containers that differs from a current allocation of the medications in the medication containers. The instructions also direct the processors to direct a change in the current allocation of the medications in the medication containers to increase a distribution velocity at which the medications are dispensed from the pharmacy dispensing system.

In one embodiment, a method includes identifying medications to be dispensed from medication containers within filling cabinets in a pharmacy dispensing system. The medication containers within the filling cabinets include separate medication containers each holding a different group of the medications. The medications are automatically dispensed from the medication containers into pill containers. The method also includes determining a distribution parameter for the medication containers. The distribution parameter represents a quantity of the medications that is dispensed and/or a limit on dispensing the medications. The method also includes determining at least one allocation of the medications in the medication containers that differs from a current allocation of the medications in the medication containers, and changing the current allocation of the medications in the medication containers to increase a distribution velocity at which the medications are dispensed from the pharmacy dispensing system. The current allocation is changed such that a different number of the medication containers holds the same medication.

BRIEF DESCRIPTION OF THE DRAWINGS

In the drawings, reference numbers may be reused to identify similar and/or identical elements.

DETAILED DESCRIPTION

Example systems and methods for automated pharmaceutical dispensing are described. In the following description, for purposes of explanation, numerous specific details are set forth in order to provide a thorough understanding of example embodiments. It will be evident, however, to one of ordinary skill in the art that these embodiments may be practiced without these specific details.

Generally, a prescription order is generated for a high-volume pharmacy. The prescription order may include more than one prescription drug for fulfillment. Each prescription drug in a prescription order is an order component of the prescription order. Generally, the order components are pill containers or other packaging having a measured quantity of a prescription medication therein. These pill containers may be filled by a fully automated process. Various factors may affect the availability of filling drugs through these processes in a pharmacy. A more fully automated process may be employed in a mail order pharmacy to fill pill containers with most frequently used drugs.

Figure 1:
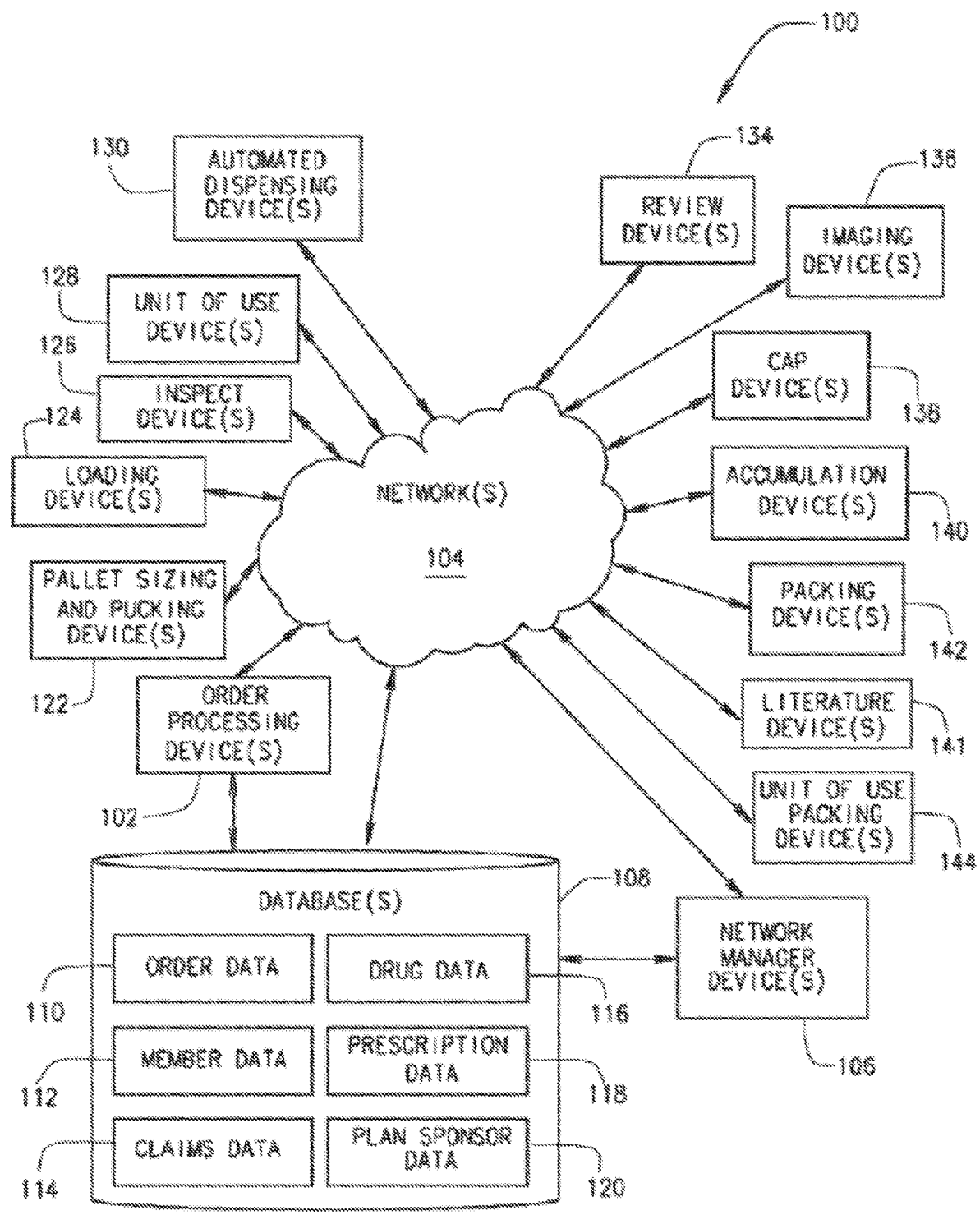
FIG. 1 is a block diagram of one example of a prescription medication dispensing system.

FIG. 1 is a block diagram of one example of a prescription medication dispensing system 100. While the system 100 is generally described as being deployed in a high-volume pharmacy (e.g., a mail order pharmacy, a direct delivery pharmacy, an automated pharmacy, and the like), the system 100 may otherwise be deployed in a location that does not administer large volumes of medication. For example, a high-volume pharmacy may dispense medication for thousands of prescription orders in one day, while a low volume pharmacy may dispense medication for dozens or hundreds of prescription orders in one day.

The system 100 may include an order processing device 102 that communicates with a benefit manager device 106 over one or more computerized communication networks 104. While the system 100 shows a single network 104, multiple networks can be used. The multiple networks may communicate in series with each other to link the devices in parallel or to otherwise link the devices shown in FIG. 1. Multiple devices may share processing and/or memory resources. The devices may be located in the same area or in different locations. For example, the devices may be located in a building or set of adjoining buildings. The devices may be interconnected (e.g. by conveyors), networked, and/or otherwise in contact with one another or integrated with one another e.g., at the high-volume fulfillment center. In addition, the functionality of a device may be split among a number of discrete devices and/or combined with other devices.

The order processing device 102 can receive requests or orders for various medications to be dispensed by the dispensing system 100 from the benefit manager device 106 and/or other sources. Additional devices which may be in communication with the benefit manager device 106 and/or the order processing device 102 over the networks 104 include one or more databases 108 which may store one or more than one of order data 110, member data 112, claims data 114, drug data 116, prescription data 118, and plan sponsor data 120; pallet sizing and pucking device(s) 122; loading device(s) 124; inspect device(s) 126; unit of use device(s) 128; automated dispensing device(s) 130; review device(s) 134; imaging device(s) 136; cap device(s) 138; accumulation device(s) 140; literature device(s) 141; packing device(s) 142; and unit of use packing device(s) 144. The system 100 may also include additional devices, which may communicate with each other via the networks 104 or directly.

The system 100 may include a single database, or multiple databases, maintained by respective devices operated by or on behalf one or a number of different persons and/or organizations. The communication may occur directly (e.g., through local storage) and/or through the network 104 (e.g., in a cloud configuration or software-as-a-service) with a device that stores a respective database.

The order processing device 102 may receive information about prescriptions being filled at a pharmacy in which the order processing device 102 is deployed. In general, the order processing device 102 is a device located within or otherwise associated with a pharmacy location to enable fulfillment of a prescription by dispensing prescription drugs. In some embodiments, the order processing device 102 may be a device that is separate from a pharmacy and that enables communication with other devices located within a pharmacy. For example, the order processing device 102 may be in communication with another order processing device 102 and/or other devices 122-144 located with a pharmacy. In some embodiments, an external pharmacy order processing device 102 may have limited functionality (e.g., as operated by a patient requesting fulfillment of a prescription drug) when an internal pharmacy order processing device 102 may have greater functionality (e.g., as operated by a pharmacy).

The order processing device 102 may track a prescription order as the order is fulfilled. A prescription order may include one or more than one prescription to be filled by the pharmacy. The order processing device 102 may make pharmacy routing decisions and/or order consolidation decisions for a prescription order. The pharmacy routing decisions include what device or devices in the pharmacy are responsible for filling at least a portion of the prescription order, where the order consolidation decisions include whether portions of a prescription order or multiple prescription orders should be shipped together for a patient or a patient family. The order processing device 102 may operate on its own or in combination with the benefit manager device 106. The order processing device 102 may track and/or schedule the literature or other paperwork associated with each order or multiple prescription orders that are being shipped together.

Examples of the devices 102, 106 include a set-top box (STB), a receiver card, a mobile telephone, a personal digital assistant (PDA), a display device, a portable gaming unit, a tablet, and a computing system; however other devices may also be used. For example, the devices 102, 106 may include a mobile electronic device, such an IPHONE or IPAD device by Apple, Inc. mobile electronic devices powered by ANDROID by Google, Inc. and a BLACKBERRY device by Blackberry Limited. The devices 102, 106 may also include other computing devices, such as desktop computing devices, notebook computing devices, netbook computing devices, gaming devices, and the like. The devices 102, 106 may include a processor, a memory to store data and instructions, and communication functionality. Other types of electronic devices that can use rules and instructions to execute various functions may also be used.

Examples of the networks 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may include optical communications. The network 104 may be a local area network or a global communication network, such as the Internet. Other conventional and/or later developed wired and wireless networks may also be used. In some embodiments, the network 104 may include a prescribing network such as the electronic prescribing network operated by Surescripts of Arlington, Va.

The benefit manager device 106 is a device operated by an entity at least partially responsible for creation and/or management of the pharmacy or drug benefit. While this benefit manager operating the benefit manager device 106 is typically a pharmacy benefit manager (PBM), other entities may operate the benefit manager device 106 either on behalf of themselves, the pharmacy benefit manager, or another entity. For example, the benefit manager may be operated by a health plan, a retail pharmacy chain, a drug wholesaler, a data analytics or other type of software-related company, or the like. In some embodiments, a pharmacy benefit manager that provides the pharmacy benefit may also provide one or more than one additional benefits including a medical or health benefit, a dental benefit, a vision benefit, a wellness benefit, a radiology benefit, a pet care benefit, an insurance benefit, a long-term care benefit, a nursing home benefit, and the like. The pharmacy benefit manager may, in addition to its pharmacy benefit manager operations, operate one or more than one pharmacy. The pharmacies may be retail pharmacies, mail order pharmacies, or otherwise.

In some embodiments, at least some of the functionality of the order processing device 102 may be included in the benefit manager device 106. The order processing device 102 may be in a client-server relationship with the benefit manager device 106, a peer-to-peer relationship with the benefit manager device 106, or in a different type of relationship with the benefit manager device 106.

The order processing device 102 and/or the benefit manager device 106 may be in communication directly (e.g., through local storage or peer-to-peer connection(s)) and/or through the network 104 (e.g., in a cloud configuration or software-as-a-service) with a database 108 (e.g., as may be retained in memory or otherwise). The database 108 may be deployed on the order processing device 102, the benefit manager device 106, on another device of the system 100, or otherwise. The database 108 may store order data 110, member data 112, claims data 114, drug data 116, prescription data 118, and/or plan sponsor data 120. Other data may be stored in the database 108.

The order data 110 may include data related to the order of prescriptions including the type (e.g., drug name and strength) and quantity of each prescription in a prescription order. The order data 110 may also include data used for completion of the prescription, such as prescription materials and/or the type and/or size of pill container in which the drug is or is preferably dispensed. In general, prescription materials are a type of order materials that include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like.

The order data 110 may be used by a high-volume fulfillment center to fulfill a pharmacy order. In some embodiments, the order data 110 includes verification information associated with fulfillment of the prescription in the pharmacy. For example, the order data 110 may include videos and/or images taken of (i) the prescription drug prior to dispensing, during dispensing, and/or after dispensing, (ii) the pill container (e.g., a pill bottle and sealing lid) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets used to transport prescriptions within the pharmacy may also be stored as order data 110.

The member data 112 includes information regarding the members associated with the benefit manager. The information stored as member data 112 may include personal information, personal health information, protected health information, and the like. Examples of the member data 112 include name, address, telephone number, e-mail address, prescription drug history, and the like. The member data 112 may include a plan sponsor identifier that identifies the plan sponsor associated with the member and/or a member identifier that identifies the member to the plan sponsor. The member data 112 may include a member identifier that identifies the plan sponsor associated with the patient and/or a patient identifier that identifies the patient to the plan sponsor. The member data 112 may also include, by way of example, dispensation preferences such as type of label, type of cap, message preferences, language preferences, or the like. The member data 112 may be accessed by various devices in the pharmacy, e.g., the high-volume fulfillment center, to obtain information utilized for fulfillment and shipping of prescription orders. In some embodiments, an external order processing device 102 operated by or on behalf of a member may have access to at least a portion of the member data 112 for review, verification, or other purposes.

In some embodiments, the member data 112 may include information for persons who are patients of the pharmacy but are not members in a benefit plan being provided by the benefit manager. For example, these patients may obtain drug directly from the pharmacy, through a private label service offered by the pharmacy, the high-volume fulfillment center, or otherwise. In general, the use of the terms member and patient may be used interchangeably herein.

The claims data 114 includes information regarding pharmacy claims adjudicated by the pharmacy benefit manager under a drug benefit program provided by the pharmacy benefit manager for one, or more than one, plan sponsors. In general, the claims data 114 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility. Additional information may be included. In some embodiments, other types of claims beyond prescription drug claims may be stored in the claims data 114. For example, medical claims, dental claims, wellness claims, or other type of health care-related claims for members may be stored as a portion of the claims data 114.

In some embodiments, the claims data 114 includes claims that identify the members with whom the claims are associated. In some embodiments, the claims data 114 includes claims that have been de-identified (e.g., associated with a unique identifier but not with a particular, identifiable member).

The drug data 116 may include drug name (e.g., technical name and/or common name), other names by which the drug is known by, active ingredients, an image of the drug (e.g., in pill form), and the like. The drug data 116 may include information associated with a single medication or multiple medications.

The prescription data 118 may include information regarding prescriptions that may be issued by prescribers on behalf of patients, who may be members of the drug benefit plan, for example to be filled by a pharmacy. Examples of the prescription data 118 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 110 may be linked to associated member data, claims data 114, drug data 116, and/or prescription data 118.

The plan sponsor data 120 includes information regarding the plan sponsors of the benefit manager. Examples of the plan sponsor data 120 include company name, company address, contact name, contact telephone number, contact e-mail address, and the like.

The order processing device 102 may direct at least some of the operations of the devices 122-144, recited above. In some embodiments, operations performed by one of these devices 122-144 may be performed sequentially, or in parallel with the operations of another device as may be coordinated by the order processing device 102. In some embodiments, the order processing device 102 tracks a prescription with the pharmacy based on operations performed by one or more of the devices 122-144.

In some embodiments, the system 100 may transport pill containers (e.g., between one or more than one of the devices 122-144 in the high-volume fulfillment center) by use of pallets. The pallet sizing and pucking device 122 may configure pucks in a pallet. A pallet may be a transport structure for a number of pill containers and may include a number of cavities. A puck may be placed in one or more than one of the cavities in a pallet by the pallet sizing and pucking device 122. A puck may include a receptacle sized and shaped to receive a pill container. Such pill containers may be supported by the pucks during carriage in the pallet and during movement through the fulfillment process. Different pucks may have differently sized and shaped receptacles to accommodate pill containers of different sizes, as may be appropriate for different prescriptions. Pucks allow the standardization of equipment engaging differently sized pill containers such that some automated equipment can move the pill container by gripping the puck that is supporting the pill container and allow the use of a standardized pallet that holds a plurality of pucks have a same outer dimension while having differently sized receptacles therein to hold differently sized pill containers. The pucks may also operate to ensure that a pill container is centered in a location on the pallet.

The arrangement of pucks in a pallet may be determined by the order processing device 102 based on prescriptions which the order processing device 102 decides to launch. In general, prescription orders in the order database 110 reside in one or more than one queues and are generally launched in a first-in-first-out order. However, the order processing device 102 may use logic and a variety of factors to determine when and how prescriptions are to be launched. For example, some non-limiting factors which may alter the first-in-first-out order of launching prescriptions in a pharmacy include the age of the order, whether the order required an outreach to a physician or some other intervention, whether there are any performance guarantees with plan sponsors or members, the available inventory of a given pharmaceutical in view of existing prescriptions already launched which will require that pharmaceutical, the capacity of one or more manufacturing sources to produce additional units of the drugs or medications, the zip code to which the order will be shipped, the workload and volume of various parts of the pharmacy, whether valid paperwork for the order has been received, and/or similar orders for the same pharmaceutical that are already to be launched. The logic may be implemented directly in the pallet sizing and pucking device 122, in the order processing device 102, in both devices 102, 122, or otherwise. Once a prescription is set to be launched, a puck suitable for the appropriate size of pill container for that prescription may be positioned in a pallet by a robotic arm or pickers. The pallet sizing and pucking device 122 may launch a pallet once pucks have been configured in the pallet. The loading device 124 may load pill containers into the pucks on a pallet by a robotic arm, pick and place mechanism, or the like. In one embodiment, the loading device 108 has robotic arms or pickers to grasp a pill container and move it to and from a pallet. The loading device 124 may also print a label which is appropriate for a pill container that is to be loaded onto the pallet and apply the label to the pill container. The pallet may be located on a conveyor assembly during these operations. In an example embodiment, the pill containers may be positioned in the pucks by the loading device 124 prior to the pucks being placed in the pallet. The inspect device 126 may verify that pill containers in a pallet are correctly labeled and in the correct spot on the pallet. The inspect device 126 may scan the label on one or more than one pill container on the pallet. Labels of pill containers may be scanned or imaged in full or in part by the inspect device 126. Such imaging may occur after the pill container has been lifted out of its puck by a robotic arm, picker, or the like, or may be otherwise scanned or imaged while retained in the puck. In some embodiments, images and/or video captured by the inspect device 126 may be stored in the database 108 as order data 110.

The unit of use device 128 may temporarily store, monitor, label and/or dispense unit of use products. In general, unit of use products are prescription drug products that may be delivered to a patient or member without being repackaged at the pharmacy. These products may include pills in pill container, pills in a blister pack, inhalers, and the like. Pills to be placed in a pill container may include, and not be limited to, capsules, tablets, caplets, lozenges, and other solid medium with a pharmaceutical component that may be ingested by a person or other mammal. Prescription drug products dispensed by the unit of use device 128 may be packaged individually or collectively for shipping or may be shipped in combination with other prescription drugs dispensed by other devices in the high-volume fulfillment center.

The automated dispensing device 130 may include one or more than one device that dispense prescription drugs or pharmaceuticals into pill containers in accordance with one or multiple prescription orders. In general, the automated dispensing device 130 may include mechanical and electronic components with, in some embodiments, software and/or logic to facilitate pharmaceutical dispensing that would otherwise be performed in a manual fashion by a pharmacist and/or pharmacist technician. For example, the automated dispensing device 130 may include high volume fillers that fill a number of prescription drug types at a rapid rate and blister pack machines that dispense and pack drugs into a blister pack or other pre-packaged form of pills. Prescription drugs dispensed by the automated dispensing devices 130 may be packaged individually or collectively for shipping or may be shipped in combination with other prescription drugs dispenses by other devices in the high-volume fulfillment center.

The automated dispensing device 130 may be used, for example, to dispense commonly prescribed dispense drugs in an automatic or semiautomatic method into pill containers. Drugs may be dispensed in connection with filling one or more than one prescription (or portions of prescriptions). Drugs dispensed by the automated dispensing device 130 may be tablets, pills, capsules, caplets, or other types of drugs suitable for dispensing by the automated dispensing device 130.

The review device 134 may process pill containers to be reviewed by a pharmacist for proper pill count, exception handling, prescription verification, and the like. Fulfilled prescriptions may be manually reviewed and/or verified by a pharmacist, as may be required by state or local law.

The imaging device 136 may image pill containers after they have been filled with pharmaceuticals. The imaging device 136 may measure the fill height of the pharmaceuticals in the pill container based on the obtained image to determine if the pill container is filled to the correct height given the type of pharmaceutical and the number of pills in the prescription. Images of the pills in the pill container may also be obtained to detect the size of the pills themselves and markings thereon. The images may be transmitted to the order processing device 102, and/or stored in the database 110 as part of the order data 110.

The cap device 138 may be used to cap or otherwise seal a pill container. In some embodiments, the cap device 138 may secure a pill container with a type of cap in accordance with a patient preference (e.g., a preference regarding child resistance), a plan sponsor preference, a prescriber preference, or the like. The cap device 138 may also etch a message into the cap or otherwise associate a message into the cap, although this process may be performed by a subsequent device in the high-volume fulfillment center.

The accumulation device 140 accumulates various pill containers of prescription drugs in a prescription order. The accumulation device 140 may accumulate pill containers from various devices or areas of the pharmacy. For example, the accumulation device 140 may accumulate pill containers from the unit of use device 128, the automated dispensing device 130, and the review device 134, at the high-volume fulfillment center. The accumulation device 140 may be used to group the pill containers prior to shipment to the member or otherwise. In some embodiments, the literature device 141 folds or otherwise prepares the literature for inclusion with a prescription drug order (e.g., in a shipping container). In some embodiments, the literature device 141 that prints the literature may be separate from the literature device that prepares the literature for inclusion with a prescription order.

The packing device 142 packages a prescription order in preparation for shipping the order. The packing device 142 may box, bag, or otherwise package the fulfilled prescription order for delivery. The packing device 142 may further place inserts, e.g., literature or other papers into the packaging received from the literature device 141 or otherwise. For example, bulk prescription orders may be shipped in a box, while other prescription orders may be shipped in a bag which may be a wrap seal bag. The packing device 142 may label the box or bag with the address and a recipient's name. The label may be printed and affixed to the bag or box, be printed directly onto the bag or box, or otherwise associated with the bag or box. The packing device 142 may sort the box or bag for mailing in an efficient manner (e.g., sort by delivery address). The packing device 142 may include ice or temperature sensitive elements for prescriptions which are to be kept within a temperature range during shipping in order to retain efficacy or otherwise. The ultimate package may then be shipped through postal mail, through a mail order delivery service that ships via group and/or air (e.g., UPS, FEDEX, or DHL), through delivery service, through a local delivery service (e.g., a courier service), through a locker box at a shipping site (e.g., an AMAZON locker or a post office box), or otherwise.

The unit of use packing device 144 packages a unit of use prescription order in preparation for shipping the order. The unit of use packing device 144 may include manual scanning of pill containers to be bagged for shipping to verify each pill container in the order. In an example embodiment, the manual scanning may be performed at a manual station.

While the system 100 in FIG. 1 is shown to include single devices, multiple devices may be used. The devices shown in FIG. 1 may be the same type or model of device or may be different device types or models. When multiple devices are present, the multiple devices may be of the same device type or models or may be a different device type or model. The types of devices shown in FIG. 1 are examples of devices and, in other configurations of the system 100, lesser, additional, or different types of devices may be included.

Figure 2:
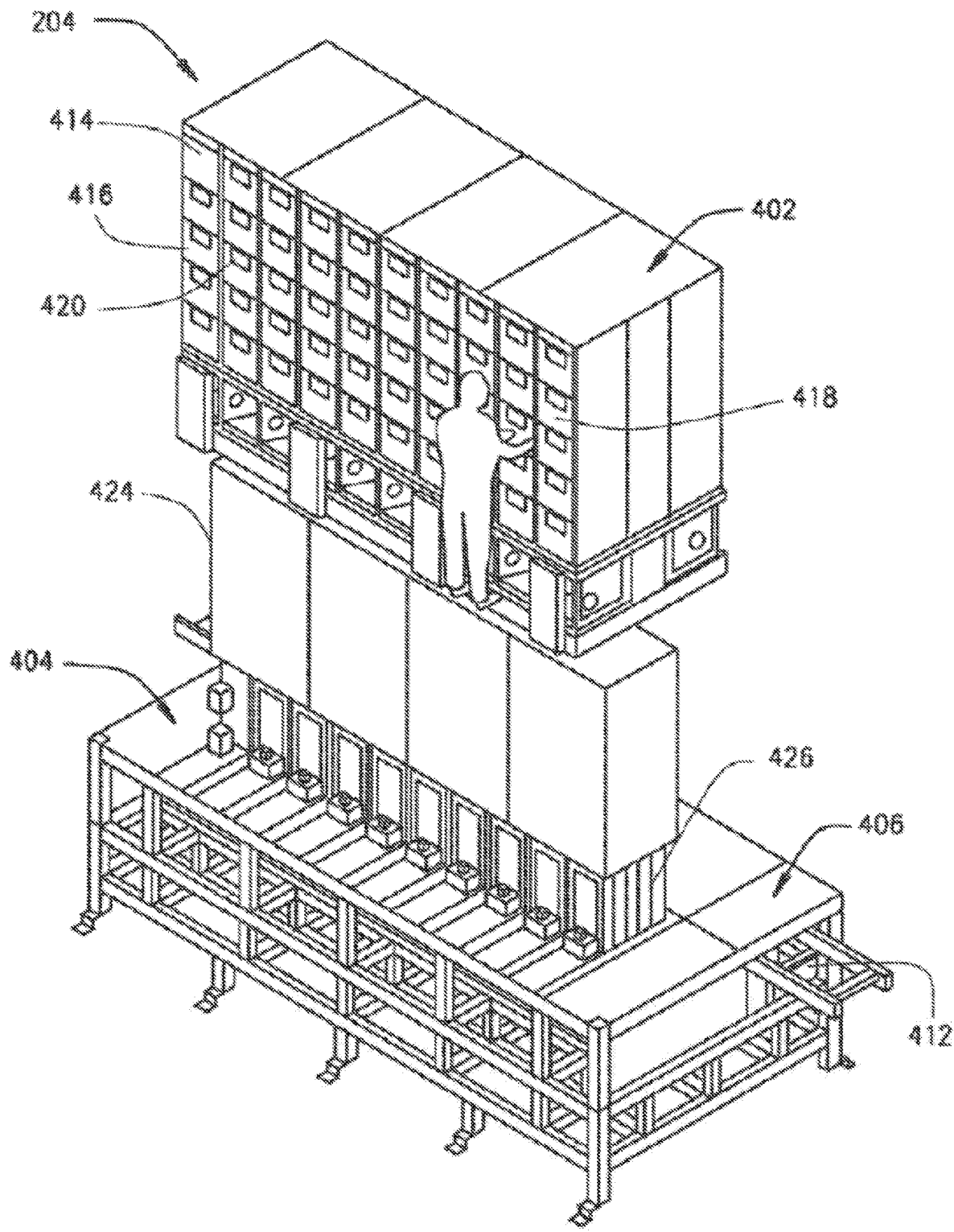
FIG. 2 illustrates the automated dispensing subsystem shown in FIG. 1 according to an example embodiment.
Figure 3:
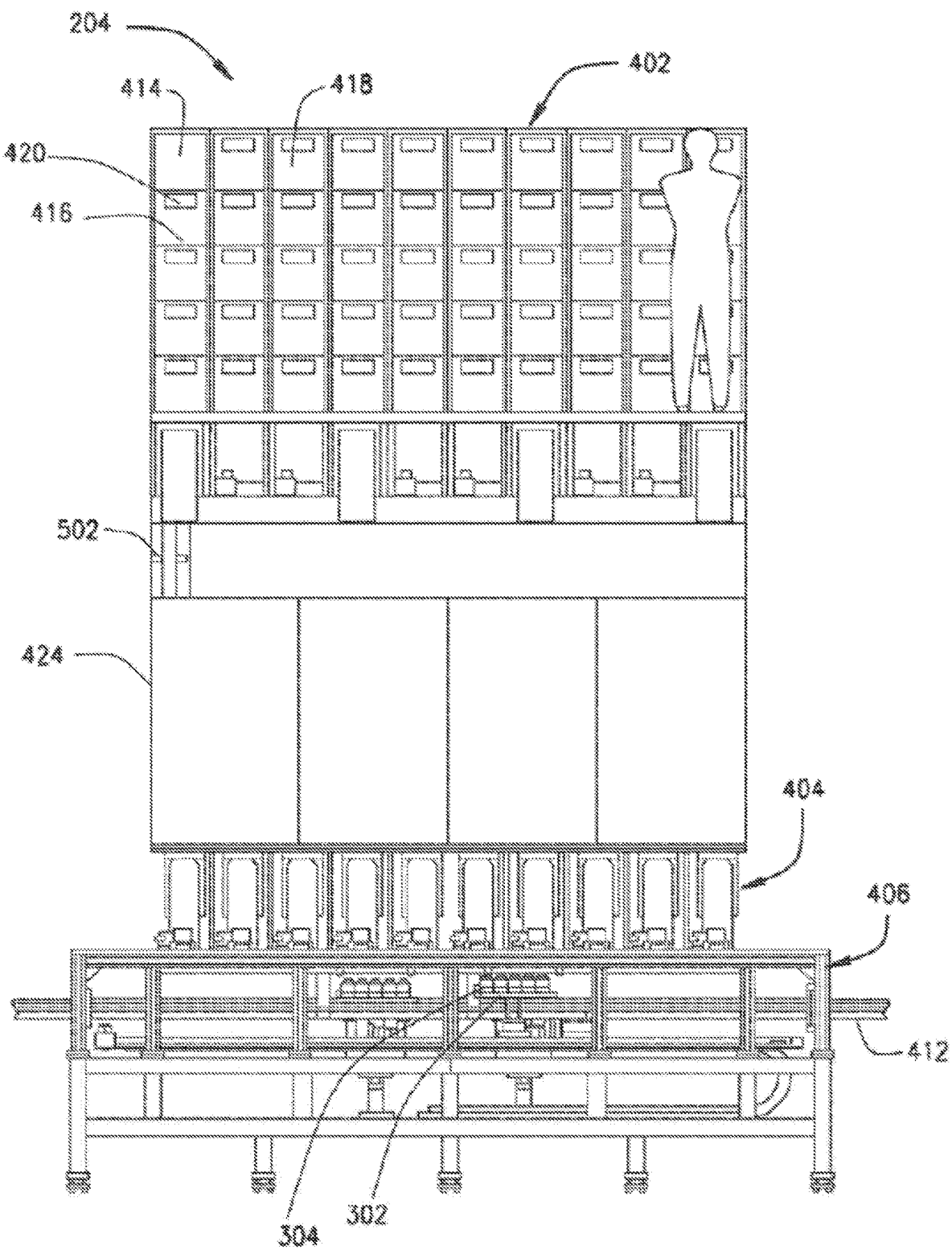
FIG. 3 also illustrates the automated dispensing subsystem shown in FIG. 1 according to an example embodiment.
Figure 4:
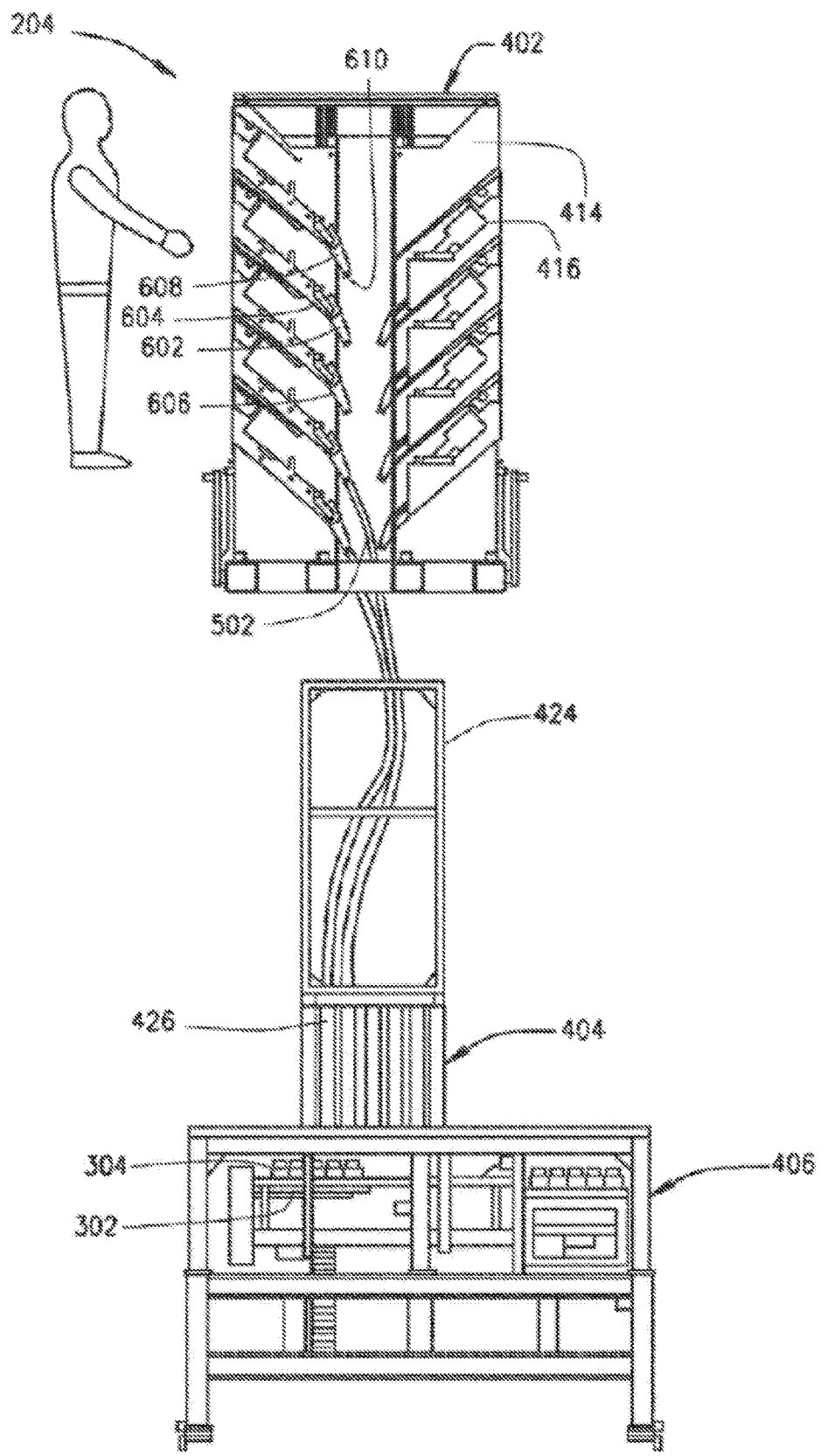
FIG. 4 also illustrates the automated dispensing subsystem shown in FIG. 1 according to an example embodiment.

FIGS. 2 through 4 illustrate the automated dispensing subsystem 204, according to an example embodiment. The automated dispensing subsystem 204 may be deployed within the automated dispensing device 130 or may otherwise be deployed. The automated dispensing subsystem 204 enables dispensing of a number of different types of pharmaceuticals in an automatic or semiautomatic manner.

The automated dispensing subsystem 204 includes a filling cabinet 402, a prefill assembly 404, and a pallet assembly 406. The filling cabinet 402 optionally can be referred to as a tower. The filling cabinet 402 stores pharmaceuticals to be dispensed into pill containers 304 via the prefill assembly 404 and dispenses measured quantities of pharmaceuticals into the prefill assembly 404. The prefill assembly 404 stores the measured quantities of pharmaceuticals and dispenses the measured quantities of pharmaceuticals received from the filling cabinet 402 into pill containers 304 on pallets 302 while in the pallet assembly 406.

A pallet conveyor 412 may transport the pallets 302 through some or all of the devices within the system 100, such as the automated dispensing device 130. The pallet assembly 406 receives the pallets 302 via the pallet conveyor 412 and moves the pallets 302 within the pallet assembly 406 such that pharmaceuticals dispensed by the automated dispensing subsystem 204 are dispensed into the pill containers 304 on the pallet 302.

The filling cabinet 402 may be physically housed, located, positioned or installed above the prefill assembly 404 and the pallet assembly 406. For example, the filling cabinet 402 may be located on a first floor (e.g., in a building) and the prefill assembly 404 and the pallet assembly 406 may be located on a second floor (e.g., in the same building) below the filling cabinet 402. These components of the automated dispensing subsystem 204 may be otherwise positioned, e.g., in a position to utilize gravity to move pharmaceuticals from the filling cabinet 402 to the prefill assembly 404 and then to the pill containers 304 in the pallet 302. For example, some portion of the filling cabinet 402 may extend below the first floor.

The filling cabinet 402 may include multiple medication containers, which also can be referred to as cells. The medication containers 414 may each be adapted to hold different pharmaceuticals. For example, different medication containers 414 in the tower or cabinet 402 may hold different pharmaceuticals. The medication containers 414 differ from pill containers 304 or other individual consumer vessels that are normally used to hold several units of a single medication for a single patient. Instead, each medication container 414 may hold many more units of medication than a pill container 304 and may be used to dispense medication into multiple pill containers 304 to fill the multiple pill containers 304 with the medication. The medication containers 414 may be adapted to receive inserts 416. For example, the inserts 416 may be slidably inserted into the medication containers 414. The inserts 416 may be adapted to hold pharmaceuticals to be dispensed into the pill containers 304 via the automated dispensing subsystem 204. The medication containers 414 may receive pharmaceuticals, retain such pharmaceuticals, and dispense measured quantities of such pharmaceuticals into the prefill assembly 404. The insert 416 may be adapted to be removably received within the medication container 414. For example, the insert 416 may pull out of the medication container 414 like a drawer or a fixable pouch. In some embodiments, the medication containers 414 and the inserts 416 may be provided on opposite sides of the filling cabinet 402. Thus, the first and second sides of the filling cabinet 402 may be separately accessible. The filling cabinet 402 may include fifty medication containers 414 per side, so in an embodiment in which medication containers 414 are provided on opposite sides of the filling cabinet 402, the filling cabinet 402 may include up to and including one hundred medication containers 414. In other embodiments, fewer or more than fifty medication containers may be included per side and/or fewer or more than one hundred medication containers may be included per filling cabinet 402. Each medication container 414 may receive an insert 416 filled (or to be filled) with a different pharmaceutical or multiple medication containers 414 may each receive an insert 416 filled (or to be filled) with the same pharmaceutical. For example, more than one insert 416 may be filled with a commonly prescribed pharmaceutical.

The insert 416 may include a face plate 418 with a door 420. The door 420 may be adapted to lock and to unlock to be opened. For example, the door 420 may be adapted to be locked unless and until it is unlocked. The door 420 may be adapted to unlock pursuant to a process that mitigates risk of unauthorized access to the pharmaceuticals within the insert 416 and/or to mitigate risks that unintended pharmaceuticals will be added to the insert 416. In an example embodiment, the door 420 of the medication container 414 will unlock when identifying information is detected (e.g., by a pharmacist using a hand-held scanning device to read a bar code or other computer-readable element) that matches identifying information associated with the medication container 414 (e.g., by a pharmacist using a hand-held scanning device to read a bar code or other computer-readable element on the face plate 418 of the insert 416) and information about the pharmacist who fills the medication container 414 (e.g., by a pharmacist using a hand-held scanning device to read a bar code or other computer-readable element on the pharmacist's badge). The inserts 416 may be otherwise accessed to receive pharmaceuticals to be held and dispensed.

Figure 6:
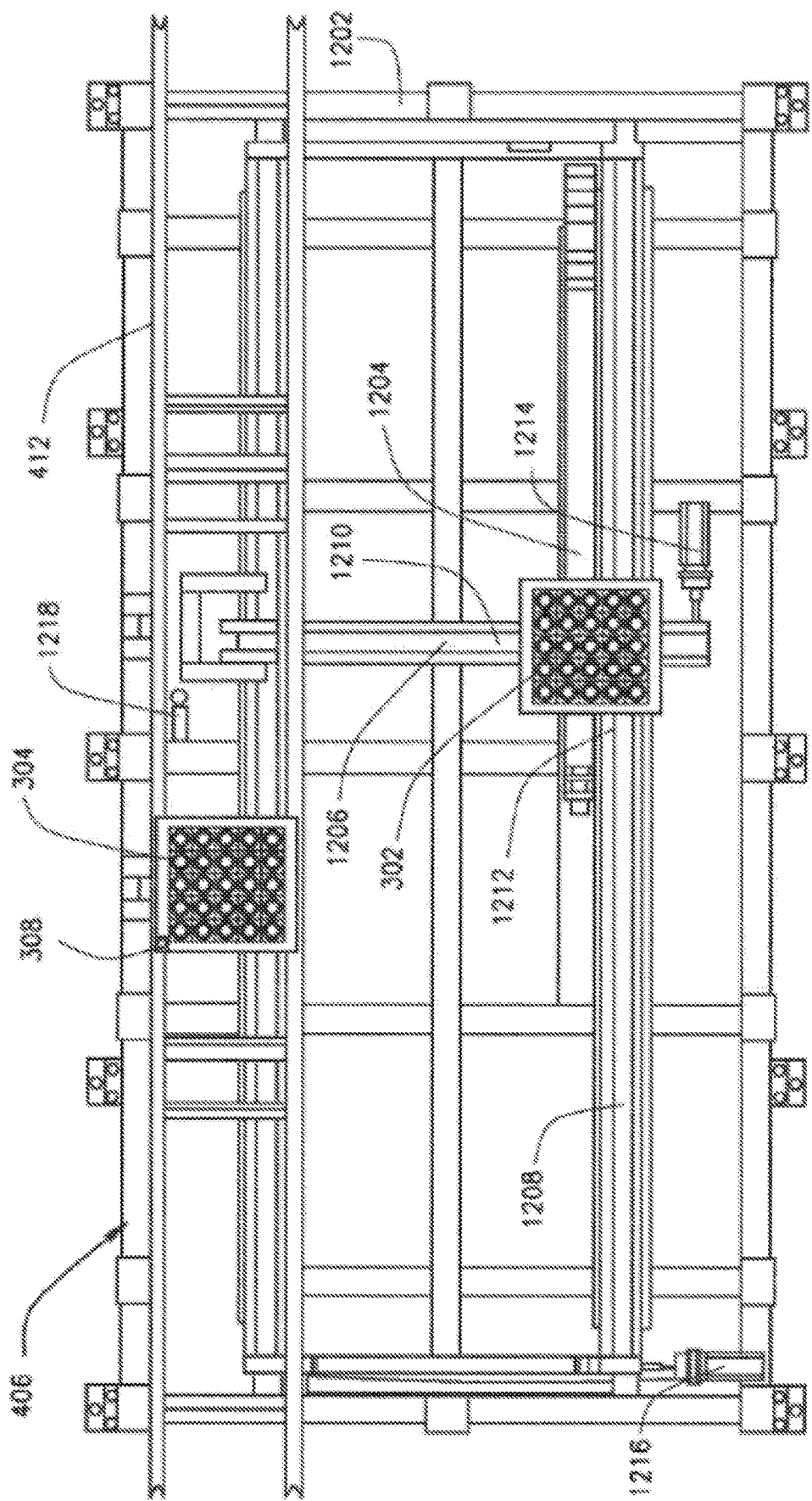
FIG. 6 illustrates a top view of a pallet assembly of the automated dispensing subsystem shown in FIG. 1, according to an example embodiment.

The medication container 414 may be adapted to receive a funnel 602. A first portion 606 of the funnel 602 disposed within the medication container 414 may be adapted to receive a dispensing tube 604 of the insert 416, through which pharmaceuticals may be dispensed from the insert 416 into the funnel 602. This may be through the large opening in the funnel 602. A second portion 608 of the funnel 602 may exist outside of the medication container 414 and be in communication with a tube 502 connected to a rear opening 610 of the funnel 602, e.g., as illustrated in FIG. 6. The second portion 608 may be the stem of the funnel 602, which acts as a discharge for the pharmaceuticals being dispensed.

Figure 5:
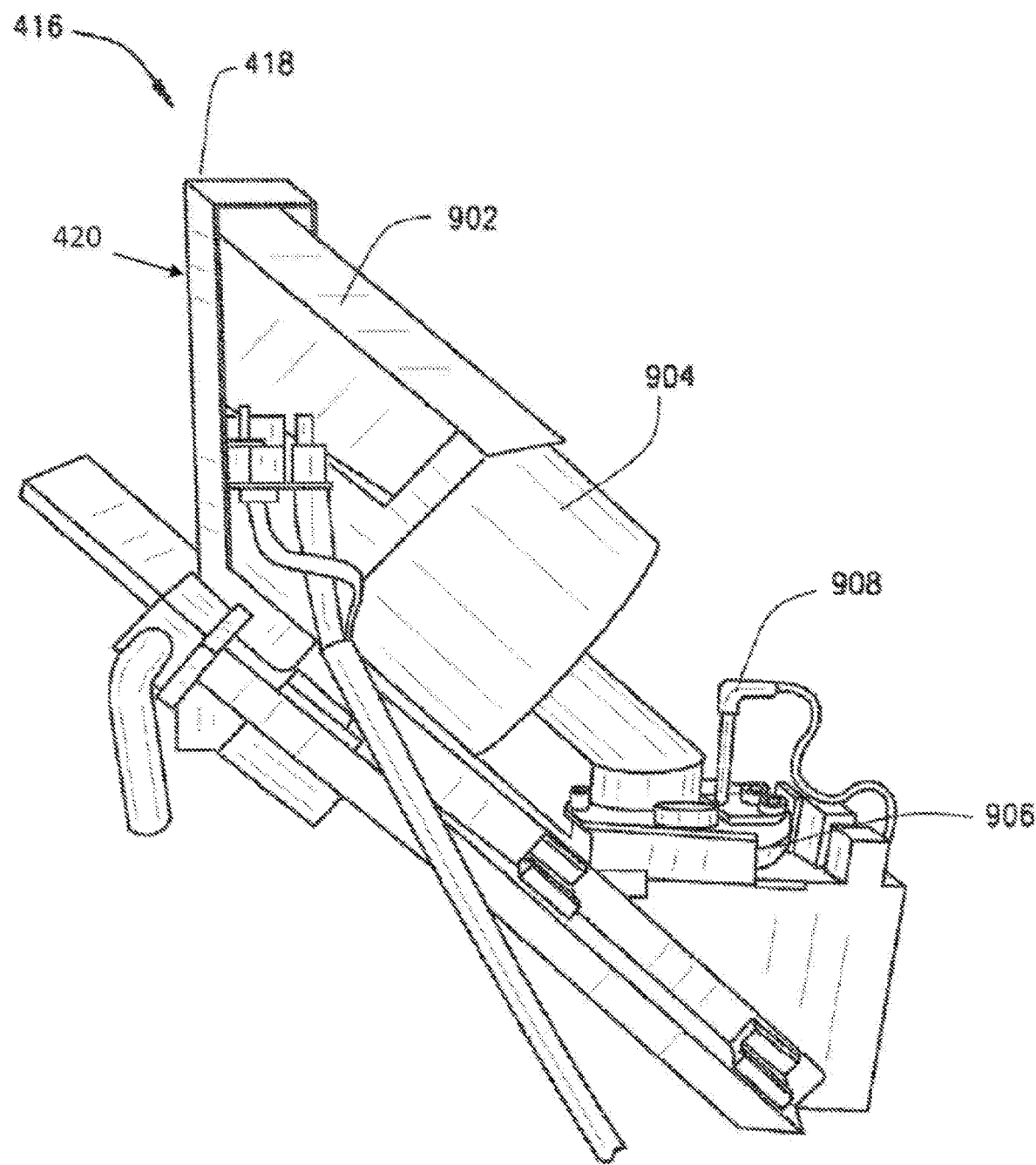
FIG. 5 illustrates an insert according to an example embodiment.

A frame portion 424 supports multiple tubes 502 connected to the discharge of the funnels 602 of the filling cabinet 402. For purposes of viewability, FIGS. 5 and 6 illustrate just two tubes 502. In general, however, the tubes 502 are included to enable the medication containers 414 to dispense drugs. The tubes 502 may be static dissipative flex tubes and may be grounded to allow for static to flow to ground the tubes 502.

The prefill assembly 404 includes multiple buffer tubes 426. Each of the tubes 502 is connected to a buffer tube 426 of the prefill assembly 404. The buffer tube 426 may be removable to, for example, facilitate cleaning or replacement. The buffer tube 426 may be shaped as a long-draw funnel or include a long-draw funnel. A long draw funnel may facilitate dispensing of pharmaceuticals while minimizing or reducing jams (relative to having a shorter or no draw funnel). In an example embodiment, a long draw funnel may be greater than six inches in length, greater than a foot in length, or greater than two feet in length and decrease in diameter over at least a portion of its length. However, the long draw funnel will maintain a diameter than will allow a pharmaceutical to pass therethrough.

The pharmaceuticals may be dispensed from the buffer tube 426 into a pill container 304 disposed on the pallet 302 when the pill container 304 is held under the buffer tube 426 within the pallet assembly 406.

FIG. 5 illustrates an insert 416 according to an example embodiment. A chute 902 may be in communication with a door 420 on a face plate 418 of the insert to receive pharmaceuticals, e.g., when the insert 416 is filled by a pharmacist. The chute 902 may empty into a rotating hopper 904 in communication with a vibratory bowl 906. A level sensor 908 may be adapted to receive information about the quantity of pharmaceuticals in the vibratory bowl 906 and/or the hopper 904. Signals from the level sensor 908 may cause the hopper to spin to release additional quantities of pharmaceuticals into the vibratory bowl 906 and/or to stop spinning.

The insert 416 may employ vibratory technologies to facilitate a rapid dispensing stream of pharmaceuticals from the insert 416 into the funnel 602. The insert 416 may be adapted to count pharmaceuticals as units of the pharmaceuticals exit the vibratory bowl 906. Pharmaceuticals may be counted via a scanner array through which the pharmaceuticals pass as they exit the vibratory bowl 906. Pharmaceuticals may be otherwise counted. In an example embodiment, the insert 416 is a counting container canister manufactured by Kirby Lester, LLC. Other devices may be used to perform the functions of an insert 416. Counted pharmaceuticals (for example, a number of units of pharmaceuticals to be dispensed in accordance with a prescription) may be dispensed from the vibratory bowl 906 through the corresponding funnel 602 and into the corresponding tube 502 (shown in FIG. 4).

Figure 7:
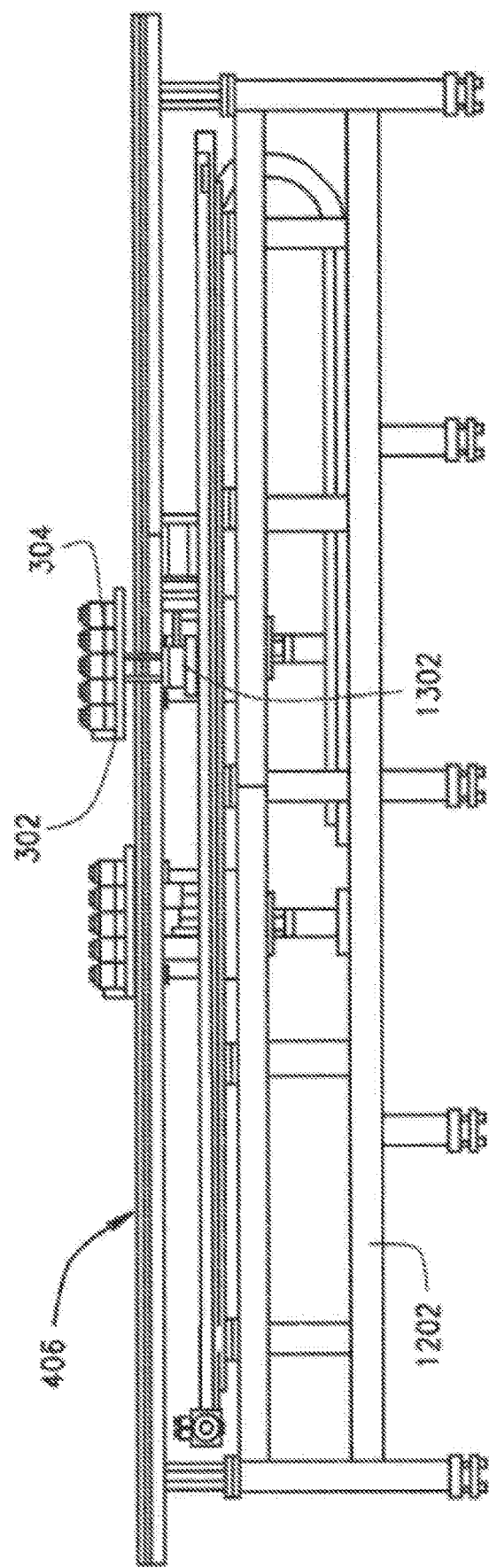
FIG. 7 illustrates a side view of a pallet assembly of the automated dispensing subsystem shown in FIG. 1, according to an example embodiment

FIGS. 6 and 7 illustrate a top view and a side view, respectively, of the pallet assembly 406 of the automated dispensing subsystem 204, according to an example embodiment. A pallet assembly frame 1202 provides support in the pallet assembly 406, including the pallet conveyor 412 and an x-y movement apparatus 1204. The x-y movement apparatus 1204 moves the pallet 302 within the pallet assembly 406 of the automated dispensing subsystem 204. The x-y movement apparatus 1204 includes an x-component 1206 and a y-component 1208. The x-component 1206 moves a pallet 302 in a direction perpendicular to the pallet conveyor 412. The x-component 1206 includes an x-axis support arm 1210 that supports the pallet 302 as it moves within the pallet assembly 406 and an x-component motor 1214 that actuates the x-component 1206 of the x-y movement apparatus 1204. The y-component 1208 moves a pallet 302 in a direction parallel to the pallet conveyor 412. The y-component 1208 includes a y-axis support arm 1212 that supports the pallet 302 as it moves within the pallet assembly 406 and a y-component motor 1216 that actuates the y-component 1208 of the x-y movement apparatus 1204.

The x-y movement apparatus 1204 may engage and move a pallet 302 within the pallet assembly 406 of the automated dispensing subsystem 204 such that the pill containers 304 in the pallet 302 are moved below the buffer tubes 426 in communication with the medication containers 414 containing pharmaceuticals to be dispensed into such pill containers 304, via the system 100.

The pallet assembly 406 may include a lift apparatus 1302. The lift apparatus 1302 may engage the pallet 302 and lift it such that a pill container 304 on the pallet 302 is aligned to receive pharmaceuticals from the buffer tube 426 in communication with the medication container 414 holding pharmaceuticals to be dispensed into that particular pill container 304. In an example, the pill container 304 is positioned directly (or substantially directly) below the buffer tube exit 1036 of the buffer tube 426 in communication with the medication container 414 holding pharmaceuticals to be dispensed into that particular pill container 304. A pill container 304 may be positioned such that the opening of the pill container 304 is very close to the buffer tube exit 1036, e.g., less than approximately 0.01 inches, 0.009 inches, 0.008 inches, 0.007 inches, 0.006 inches, 0.005 inches, or 0.004 inches from the buffer tube exit 1036.

Pharmaceuticals may be dispensed from the buffer tube 426 into the pill container 304 when the appropriate pill container 304 is held under the buffer tube exit 1036 by the lift apparatus 1218 of the pallet assembly 406. In an example embodiment, such pharmaceuticals are held in held the third holding area 1034 of the buffer tube 426 and are dispensed into the pill container 304 when the third buffer tube gate 1006 is actuated by the third switch 1018. In another example embodiment, such pharmaceuticals are held in the first or second holding area 1030, 1032 of the buffer tube 426 when the pill container 304 is position below the buffer tube exit 1036 and released through the first and/or second buffer tube gates 1002, 1004 prior to being released through the third buffer tube gate 1006 and into the pill container 304.

The automated dispensing subsystem 204 may include a radio frequency identification (RFID) reader 1218. The RFID reader 1218 may read data on the RFID tag 308 of the pallet 302 to obtain data associated with the particular pallet 302 and/or pill containers 304 within the pallet 302, such as order data 110, member data 112, claims data 114, drug data 116, prescription data 118, and/or plan sponsor data 120 associated with prescriptions (or portions of prescriptions) to be filled using pill containers 304 on that pallet 302.

The RFID reader 1218 and/or another RFID reader may read the container identifiers of the pill containers 304 to be filled at the automated dispensing subsystem 204 and the identifiers of the particular containers from which the pill containers 304 will be filled from the RFID tag 308 of the pallet 302 when it enters the automated dispensing subsystem 204. The RFID reader 1218 and/or another RFID reader may read the pallet route within the system 100 and the pallet route within the automated dispensing subsystem 204 as it exits the automated dispensing subsystem 204 and may clear the pallet route within the automated dispensing subsystem 204 as it exits the automated dispensing subsystem 204 (e.g., to prevent the pallet 308 from re-entering the same automated dispensing subsystem 204 in an embodiment of the system 100 that employs more than one automated dispensing subsystem 204).

Figure 8:
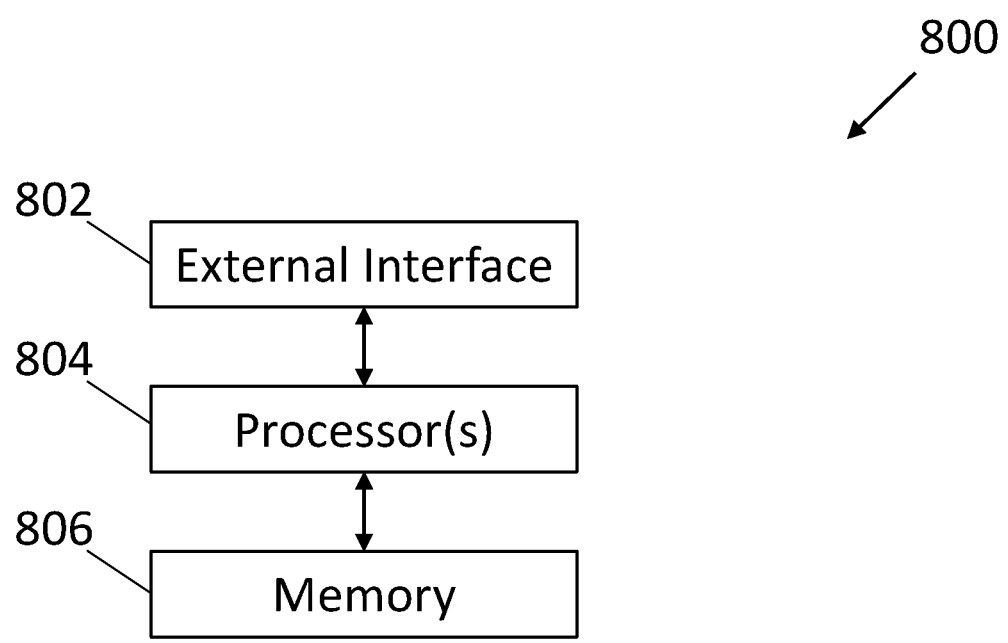
FIG. 8 illustrates one embodiment of a management system that allocates medication in a dispensing system, such as the prescription medication dispensing system.

FIG. 8 illustrates one embodiment of a management system 800 that allocates medication in a dispensing system, such as the prescription medication dispensing system 100. The management system 800 can monitor various distribution parameters of one or more filling cabinets 402 and/or medication containers 414 in the one or more filling cabinets 402, analyze these distribution parameters, and determine how to allocate different medications among two or more filling cabinets 402 to optimize (e.g., improve) a throughput velocity of the prescription medication dispensing system 100.

This optimization can involve increasing a distribution velocity of the system 100. The distribution velocity is a measure of a rate at which units of medication or pharmaceuticals are dispensed from the medication containers 414 into containers (e.g., pill containers) per unit time (e.g., per day, per hour, per minute, or the like). The distribution velocity can be improved by increasing the distribution velocity relative to another, different allocation of the medications in the medication containers 414 among the cabinets 402.

An allocation of medications (also referred to herein as pharmaceuticals) can represent or indicate which medications are in the medication containers 414 in different cabinets 402. Optionally, the allocation can alternatively include or can additionally include a representation or indication of how many different medication containers 414 in the same cabinet 402 have the same medication (e.g., the same chemical compound and the same unit dosage amount). Stated differently, the allocation that is determined can indicate which medications are in the medication containers 414 of different cabinets 402 and/or how many medication containers 414 in each cabinet 402 have the same medication.

The management system 800 can monitor the distribution parameters of a filling cabinet 402 and determine which medication should be in the medication containers 414 of different cabinets 402 in the same facility. Certain allocations of the medications in the medication containers 414 can result in the distribution velocity increasing, while other allocations can result in a non-increasing or a decreasing distribution velocity.

Once the management system 800 determines the medication allocation for the cabinets 402, the management system 800 can generate an output signal that is communicated to one or more persons that fill the medication containers 414 in the cabinets 402 to direct which medications are to be in which medication containers 414. Optionally, this signal can be sent to an automated (e.g., robotic) system that automatically fills the medication containers 414 with medications per the output signal.

The management system 800 includes an external interface 802 that represents hardware circuitry that communicates with one or more sensors or other sources of information to obtain or determine the distribution parameters. The external interface 802 can represent communication circuitry, such as one or more connectors, modems, switches, antennas, or the like, that communicate with sensors such as the level sensor 908, the scanner array, or the like. These sensors can communicate signals to the external interface 802 that indicate how many units of different medications are being distributed from the different medication containers 414. The external interface 802 can obtain these signals and send the signals to one or more processors 804 of the management system 800 and/or to a tangible and non-transitory computer readable medium, such as one or more computer memories 806. The processors 804 represent hardware circuitry that includes and/or is connected with one or more microprocessors, field programmable gate arrays, and/or integrated circuits. The memories 806 can represent computer hard drives, optical discs, or the like.

The distribution parameters can be measured aspects of the filling of containers with medications, can be derived from these measured aspects, and/or can be limits imposed on the amount of medications in the containers. With respect to the measured aspects, the distribution parameters can include how many units of each type of medication is distributed (e.g., placed into medication containers from the medication containers 414) per unit time (e.g., every day, every hour, every minute, etc.). Another measured distribution parameter can be a count of how many containers are filled with the same medication (from the same medication container 414 and/or from different medication containers 414) per unit time or within a designated period of time (e.g., every day, every hour, every minute, etc.). Another measured distribution parameter can be a count of how many medication containers 414 in the same cabinet 402 include the same medication. Another measured distribution parameter can be a count of how many medication containers 414 in different cabinets 402 include the same medication.

A medication container 414 may be offline or otherwise unable to distribute medication when the medication container 414 is depleted of medication or when the medication container 414 has an insufficient number of units of a medication to fill a prescription order. The medication container 414 in a cabinet 402 can be offline until the medication container 414 is replenished with the medication. The medication container 414 may be offline and unable to distribute the medication until the medication container 414 is replenished. If the depleted medication container 414 is the only medication container 414 in the cabinet 402 that has the medication, then no more of that medication can be distributed from that cabinet 402 until the medication container 414 is replenished with the medication. This can result in significant downtime in the system 100.

The distribution parameters optionally can include an indication or count of how many times a medication container 414 in a cabinet 402 is offline due to a need for replenishment of medication. This count may be the number of times that the medication container 414 is offline per unit time, such as per day, per hour, or the like. This count may be determined by the processors 804 examining the amount of medication units reported as being in the medication container 414 and/or distributed from the medication container 414 from the level sensor 908, the scanner array, or the like. For example, if a medication container 414 is sized to hold 1,000 units of a medication and the level sensor 908 communicates a signal indicating that the medication container 414 has zero units of medication or the scanner array communicates a signal indicating that the medication container 414 has dispensed 1,000 units of the medication, then the processors 804 can determine that the medication container 414 is depleted and offline.

The distribution parameters optionally can include limits on the system 100. A distribution parameter can include a lower limit or requirement on the number (and/or identity) of different types of medications to be dispensed from the cabinets 402. For example, each cabinet 402 may have a requirement to include a designated number of medication containers 414 storing and dispensing a designated list of medications. These can include medications that are commonly prescribed and that are more likely to be dispensed in greater volumes than other, less commonly prescribed medications.

A distribution parameter can include an upper limit on the units of a medication that can be dispensed from a medication container 414. For example, some medication units may be relatively large and, as a result, fewer units can fit inside a medication container (e.g., a pill container). As another example, some laws or regulations may restrict how many units of a medication can be dispensed in a prescription order.

Another example of a distribution parameter is a co-morbidity relationship between medications. Certain medications may be prescribed to the same patient or group of patients more often than other combinations of medications. Therapeutic information associated with medications can indicate which combinations of multiple medications or medication classes are associated with the same prescription drug therapy. For example, cholesterol-reducing medications may be prescribed with blood pressure-reducing medications and/or diabetic medications more often than other types of medications. If one medication in a co-morbidity relationship is distributed at a high velocity, then the other medication(s) in the same relationship may need to be kept in the same filling cabinet 402 or otherwise closer to each other than medications having no or a smaller co-morbidity relationship. This can help with packaging the pill containers having the co-morbidity medications downstream of the filling cabinets 402. For example, after the pill containers are filled by the cabinets 402, the pill containers are sorted based on which patient is to receive the medications prior to shipping the pill containers. Filling different pill containers that are going to the same patient (due to a co-morbidity relationship between the medications in the different pill containers) from medication containers 414 in the same filling cabinet 402 can reduce the time needed to sort the pill containers for shipping. Therefore, the processors 804 can determine that medications having a co-morbidity relationship should be in containers 404 in the same filling cabinet 402.

Another distribution parameter can be a geographic region that is served with the medications in the pill containers filled by the filling cabinets 402. Different geographic regions (e.g., different ZIP codes) can have different co-morbidity relationships. For example, a geographic region having more obese patients may have different co-morbidity related medications than another geographic region having older patients. Different co-morbidity relationships can be associated with different geographic regions as another distribution parameter.

Another example of a distribution parameter is a capacity of a source of the drugs to manufacture additional units of the drugs. If a manufacturing source has a more limited ability to create more units of a drug (e.g., due to pending orders from the source, due to the time required to create the drug, due to shortages of available manufacturing materials for creating the drug, etc.), then the processors 804 can restrict how many medication containers 414 and/or cabinets 402 hold units of that drug. But, if a manufacturing source has a greater ability to create more units of the drug, then the processors 804 may not restrict or may determine a larger limit on how many medication containers 414 and/or cabinets 402 hold units of the drug.

Another example of a distribution parameter is dosage information for a specific medication. Different dosages of the same medication may need to be dispensed separately from the medication containers 414 and/or cabinets 402 into the pill containers 302. The dosage information can indicate that different amounts (e.g., dosages) of the same medication may need to be placed into medication containers 414 and/or cabinets 402 that are closer together than for other medications or medications having the same dosage amount.

A distribution parameter can include a medication size. The medication size indicates how large a dosage of medication is. For example, the medication size of a medication can be the length, width, height, volume, or weight of a dosage of the medication. The medication size of different medications can be used to determine the velocity of any medication being dispensed at high volumes and to compare between different medications to balance the dispensing speed between the different cabinets 402. For example, larger medications may be dispensed more slowly than smaller medications. The larger medications can be placed in medication containers 414 and/or cabinets 402 that have smaller or minimal negative impact on the velocity at which medications are dispensed.

Another distribution parameter includes vendor and supplier information. This information can indicate where various medications are obtained or coming from. This information can be used to determine vendor and supplier performance. For example, the frequency of reorders from some vendors, how quickly vendors replenish medications, etc., can be used to determine inventory levels for medications, rates at which medications are in stock (or out of stock), service levels of suppliers, etc.

Optionally, a distribution parameter can include any other information about medication that may be used to determine an optimal amount of medications to be dispensed from the filling cabinets 402.

The distribution parameter can include medication replenishment information, such as order frequency and volume. This information can be historical information about previous inventories of medications, such as frequencies at which various medications are re-ordered from vendors and/or suppliers. Other medication replenishment information includes current inventory information. The current inventory information can indicate amounts (e.g., quantity, volume, number of dosages, etc.) of medications that are currently on-hand (e.g., on-site but not necessarily in the cabinets 402). This information can be used to determine whether there is sufficient inventory of various medications to replenish the medication containers 414 with respective medications. If there is insufficient inventory of a medication in combination with the frequency at which the medication is ordered, the volume of medication that is historically dispensed, and the vendor and/or supplier information, then demand for the medication can be prioritized so that dispensing tasks can be completed according to priority.

The medication replenishment information can include information on medication recalls and/or outages. This type of information also provides insight into the availability of various medications with respect to medication inventory. This information can be a factor in determining the on-hand inventory of various medications for prioritizing what medications are dispensed to meet satisfiable demand and to schedule dispensing tasks accordingly.

The medication replenishment information can include a number of replenishment workers that are on-site. Production information regarding resource availability can be factored in as a part of the algorithm that determines which medications are to be in the various medication containers 414. One resource availability measure is the number of workers that are available to replenish medication containers 414 with more medication. The fewer the worker that are available, the longer it may take to replenish medication containers 414.

The medication replenishment information can include any other associated information around site capacity and drug replenishment that may be useful in determining whether the demand for various medications can be met on a daily basis.

The distribution parameter can include information on the historical demand for medications. This historical demand information can include member level demographics information, such as therapies used by members of a drug benefit plan, the frequency at which members utilize home delivery of medications, etc. This information can be used with other historical demand information to determine the potential demand for medications in high volume filler at an aggregated level. In contrast, more recent patient disease histories can have a higher weight or priority than historical demand information in determining which medication containers 414 include some medications.

Additional historical demand information includes daily patient orders (e.g., demand) information for the past (e.g., the prior several years). Similar to member level demographics information, this information can be used to determine potential demand for medications, whereas more recent daily patient orders have a higher weight or priority in determining which medication containers 414 are to hold which medications than older historical orders. Other historical demand information includes hourly patient orders information for the past (e.g., the prior several years). Similar to member level demographics information and daily order information (described above), this information can be used to determine potential demand for medications, whereas more recent hourly patient orders have a higher weight or priority in determining which medication containers 414 are to hold which medications than older historical orders. Optionally, any other information associated with historical orders that may be useful in determining the medication demand on an hourly and daily basis can be used.

The processors 804 can examine the distribution parameters and can determine which medications are to be in the medication containers 414 of the different cabinets 402. In one embodiment, the processors 804 can use a model to determine which medications are to be in the medication containers 414 of the different cabinets 402. This model can represent a prediction of the amount and/or rate of consumption of various medications, where the consumption of a medication indicates the amount and/or rate at which the medication is dispensed into the pill containers 302. The model factors in some or all the information described above (e.g., some or all of the distribution parameters) and evaluates the distribution parameters over time to output a forecasted demand for each medication, as well as a classification of medications that are to be included in a cabinet 402.

One example of such a model is a multiple long-short term memory (LSTM) model. This model uses different weights or priorities for how different distribution parameters impact which medication containers 414 and/or cabinets 402 are to hold which medications. For example, historical order information of a medication may have a smaller impact or be a smaller factor in determining how many medication containers 414 and which medication containers 414 are to hold the medication than other distribution parameters, such as medication replenishment information. In one embodiment, the model that is used applies or assigns a greater weight or higher priority for more recent demand and capacity information, member demographic information, and drug recalls and outages to generate a daily demand forecast for medications being dispensed. Based on this forecasted demand, medication containers 414 can be assigned to hold various medications. If the forecasted demand for a first medication is greater than that of a second medication, then more medication containers 414 can hold the first medication than the second medication. In various implementations, the different distribution parameters may be calculated according to Yuzhen Lu et al., "Simplified Gating in Long Short-term Memory (LSTM) Recurrent Neural Networks," arXiv preprint arXiv: 1701.1701.03441, 2017, the entire disclosure of which is incorporated by reference. In addition, the different distribution parameters may be calculated according to "Long Short-term memory," Wikipedia contributors. (2019, May 3). Long short-term memory. In Wikipedia, The Free Encyclopedia. Retrieved 17:05, May 8, 2019, from https://en.wikipedia.org/w/index.php?title=Long_short-term_memory&oldid=895314352, the entire disclosure of which is incorporated by reference.

Another model that can be used is an optimized filler tower model, or bin packing model. This model can use the forecasted demand described above, as well as the medication replenishment information and/or other distribution parameters to select a distribution of medications in each cabinet 402. The processors 804 can take the forecasted demand of each medication and the medications having co-morbidity relationships to create a set of weighting factors that can be used in a multi-variant knapsack problem. The processors 804 can then determine the optimal amount of medication to be placed in each medication container 414 utilizing the daily demand forecast, inventory information, the worker (e.g., resource) availability, and other associated distribution parameters that maximizes or increases throughputs of the medication from the cabinets 402 into the pill containers 304 (or that minimizes or decreases the variances between medications dispensed between the cabinets 402). In various implementations, the different distribution parameters may be calculated according to "Bin Packing problem," Wikipedia contributors. (2019, Feb. 21). Bin packing problem. In Wikipedia, The Free Encyclopedia. Retrieved 17:11, May 8, 2019, from https://en.wikipedia.org/w/index.php?title=Bin_packinig_problem&oldid=884345014, the entire disclosure of which is incorporated by reference. The distribution parameters may also be calculated according to "Knapsacks," https://developers.google.com/optimization/bin/knapsack, 2018, the entire disclosure of which is incorporated by reference.

The processors 804 optionally can factor in errors with error checks, best- and worst-case scenarios, etc., to determine which medications to put in which medication containers 414. For example, the processors 804 can determine how many unfulfilled orders would occur if, at the start of the day, there is no medication in one or more of the medication containers 414 in any of the filling cabinets 402 or, if there is a shift change and there are no resources available to replenish a medication, etc. The processors 804 can determine the impact on the rate at which pill containers 304 would be filled given the output of the models described above if one or more of these worst-case scenarios occurred. The processors 804 can change which medications are in which medication containers 414 and examine the impact of a worst-case scenario given the changed allocation of medication among the medication containers 414.

Alternatively, the processors 804 can track how much and how often various medications are dispensed by the system 100, and experiment with different allocations of these medications in the medication containers 414 of the cabinets 402. This experimentation can involve simulating how often medication containers 414 will be depleted of medication (based on previous rates at which the medication was dispensed) for different allocations of the medications in the medication containers 414. For example, if the processors 804 determine that a first medication is dispensed at a rate of 1,000 units per hour, a second medication is dispensed at a rate of 10,000 units per hour, and so on, then the processors 804 can simulate how often the medication containers 414 containing the first or second medication (or other medication) would need to be refilled based on these dispensing rates, the limits on how much medication can be dispensed at a time, how many medication containers 414 contain the first medication or the second medication in the current simulated allocation, and other distribution parameters.

As one example, the processors 804 can examine the distribution parameter of how many units of medication is distributed per unit time and increase how many medication containers 414 contain that medication for greater amounts of medication being distributed or decrease how many medication containers 414 contain that medication for fewer amounts of medication being distributed. The processors 804 can examine the count of how many pill containers are filled with the same medication and increase the number of medication containers 414 containing the medication for larger counts or decrease the number of medication containers 414 containing the medication for smaller counts. The processors 804 can examine the count of how many times a medication container 414 holding a medication is offline and increase the number of medication containers 414 containing the same medication for larger counts (or decrease the number of medication containers 414 containing the same medication for smaller counts).

The processors 804 can change the number of medication containers 414 in each cabinet 402 that hold the same medication and/or change how many different medications are held by the medication containers 414 in a cabinet 402 to increase the distribution velocity of the system 100. This change in container allocation, however, can be restricted by the limits described above. For example, a lower limit or requirement on the number (and/or identity) of different types of medications to be dispensed from the cabinets 402 may restrict how many medication containers 414 in the same cabinet 402 (or among several or all cabinets 402) can hold the same medication. If many different types of medications are required to be dispensed from a cabinet 402, then there may be fewer medication containers 414 in which the same medication can be held.

The processors 804 can examine different potential allocations of medications in the medication containers 414 of the cabinets 402 and can predict or estimate the distribution velocities of the system 100 with the different potential allocations. Based on this examination and prediction/estimation, the processors 804 can select an allocation to be implemented. This allocation can identify how many medication containers 414 in the different cabinets 402 are to include the same medication, how many medication containers 414 in the cabinets 402 are to include different medications, identities of the medications to be held in the medication containers 414 of various cabinets 402, or the like. The allocation that is selected can be the allocation having the fastest predicted distribution velocity from among the different potential allocations. Optionally, the allocation that is selected can be the allocation having the fewest medication containers 414 that are offline within a unit time (e.g., per day, per hour, or the like) from among the different potential allocations.

The processors 804 can store the distribution parameters, the potential allocations, the selected allocation, and/or the predicted distribution velocities in the memory 806 for storage and/or later retrieval. The processors 804 can generate a control signal that is communicated outside of the system 800 via the external interface 802. This control signal can indicate the selected allocation, such as by representing how many medication containers 414 in each cabinet 402 in the system 100 are to include various medications. The control signal can be communicated to an output device, such as an electronic display, a computer, or the like, to inform operators of the system 100 of the allocation of medications among the cabinets 402. Optionally, the control signal can be communicated to a robotic system that automatically fills the medication containers 414 with the medications as instructed by the selected allocation.

The processors 804 can continue monitoring the distribution parameters after the allocation of medications is changed to determine whether the allocation can be further refined or changed. This can result in an allocation that repeatedly is improved upon and/or that is able to adapt for changing circumstances (e.g., as the demand for medications changes).

Figure 9:
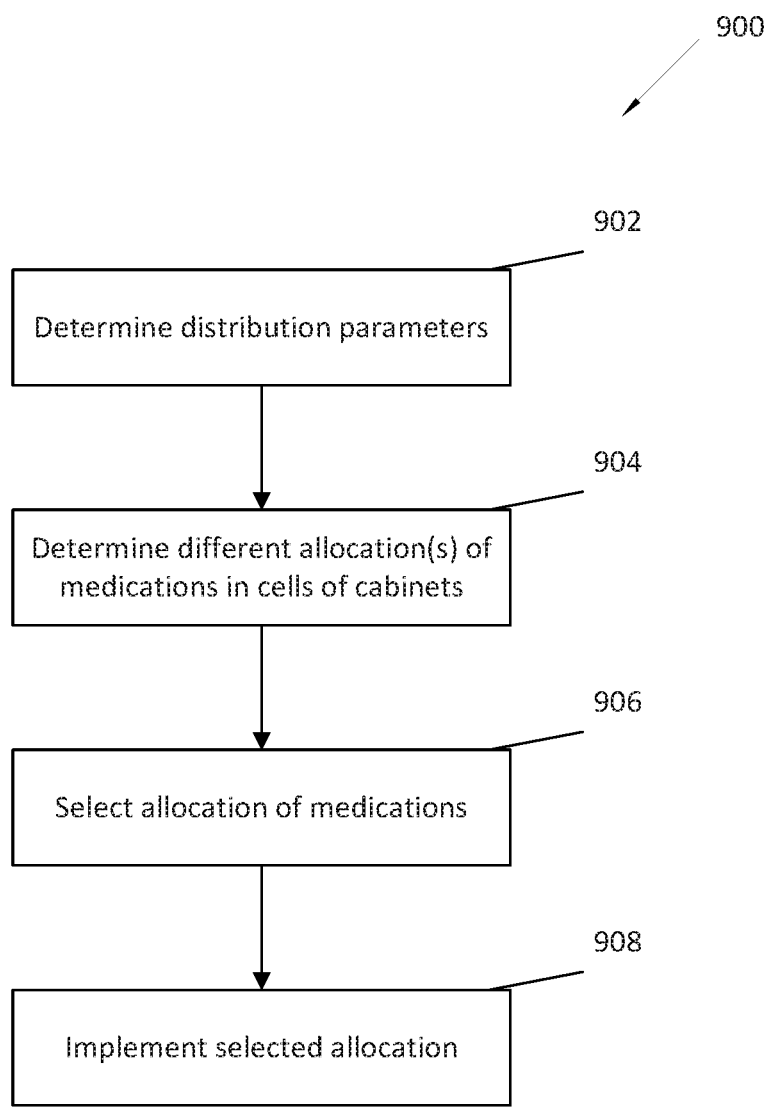
FIG. 9 illustrates a flowchart of one embodiment of a method for allocating medications among medication containers in filling cabinets of a prescription medication dispensing system.

FIG. 9 illustrates a flowchart of one embodiment of a method 900 for allocating medications among containers in filling cabinets of a prescription medication dispensing system. The method 900 can represent operations performed by the management system 800 to determine allocations of medications among the medication containers 414 of multiple filling cabinets 402 to increase the distribution velocity of medication dispensed by the prescription medication dispensing system 100. In one embodiment, the method 900 can represent the steps or operations performed by the management system 800 as directed by instructions stored in a tangible and non-transitory computer-readable storage medium (e.g., the memory 806).

At 902, one or more distribution parameters are determined. As described above, the distribution parameters can include the amount of each type of medication that is distributed, how many containers are filled with the same medication, how many containers in the same cabinet include the same medication, how many containers in different cabinets include the same medication, how many times a container is offline, a lower limit on the number of different types of medications to be dispensed, an upper limit on the units of a medication that can be dispensed from a container, co-morbidity relationships between medications, different co-morbidity relationships associated with geographic regions being served with the medications, etc. The distribution parameters can be measured, obtained from the memory, or otherwise input or determined.

At 904, a different allocation of medications in the containers of the filling cabinets is determined. In one embodiment, several different allocations may be determined. The allocations can differ by changing the medication contained in at least one container of one of the multiple cabinets in the dispensing system. The allocations can be determined to comply with the limitations and restrictions on the amount and/or variety of medications contained in the containers of the cabinets.

At 906, one of the allocations that are determined is selected. The allocation can be selected based on a predicted throughput or distribution velocity of several or all medications in the dispensing system. For example, the different allocations can be associated with different predicted distribution velocities based on how rapidly different medications previously were distributed with the current or another allocation of medications among the cabinets. The predicted distribution velocities also can be based on how many containers in the different cabinets in the different allocations have different medications. For example, an allocation having more containers with a high demand medication may have a greater distribution velocity than an allocation having fewer containers with the same high demand medication. As another example, an allocation having more containers in the same cabinet with a high demand medication and another cabinet having no or few containers with the same medication may result in a greater predicted distribution velocity as the cabinet with the greater number of containers with the high demand medication may have more containers to hold the medication so that containers that go offline can be refilled while the remaining containers continue distributing the medication.

At 908, the selected allocation is implemented. The allocation can be implemented by directing manual filling or automatically controlling automated filling of the containers in the cabinets with the medications dictated by the selected allocation. The process represented by the method 900 can be repeated one or more times to ensure that the allocation of medications among the containers in the cabinets is an efficient allocation of the medications.

By changing the allocation of medications distributed by the dispensing system, the method 900 operates to improve performance of a computerized system. For example, prior to implementing the inventive systems and methods described herein, the dispensing systems may distribute medications at a slower rate or velocity that is possible given the hardware of the dispensing systems. After implementation of the inventive systems and methods, the dispensing systems can distribute several medications at a faster throughout or distribution velocity, while avoiding or reducing downtime in containers of the cabinets, without changing or modifying any hardware components of the dispensing system.

Figure 10:
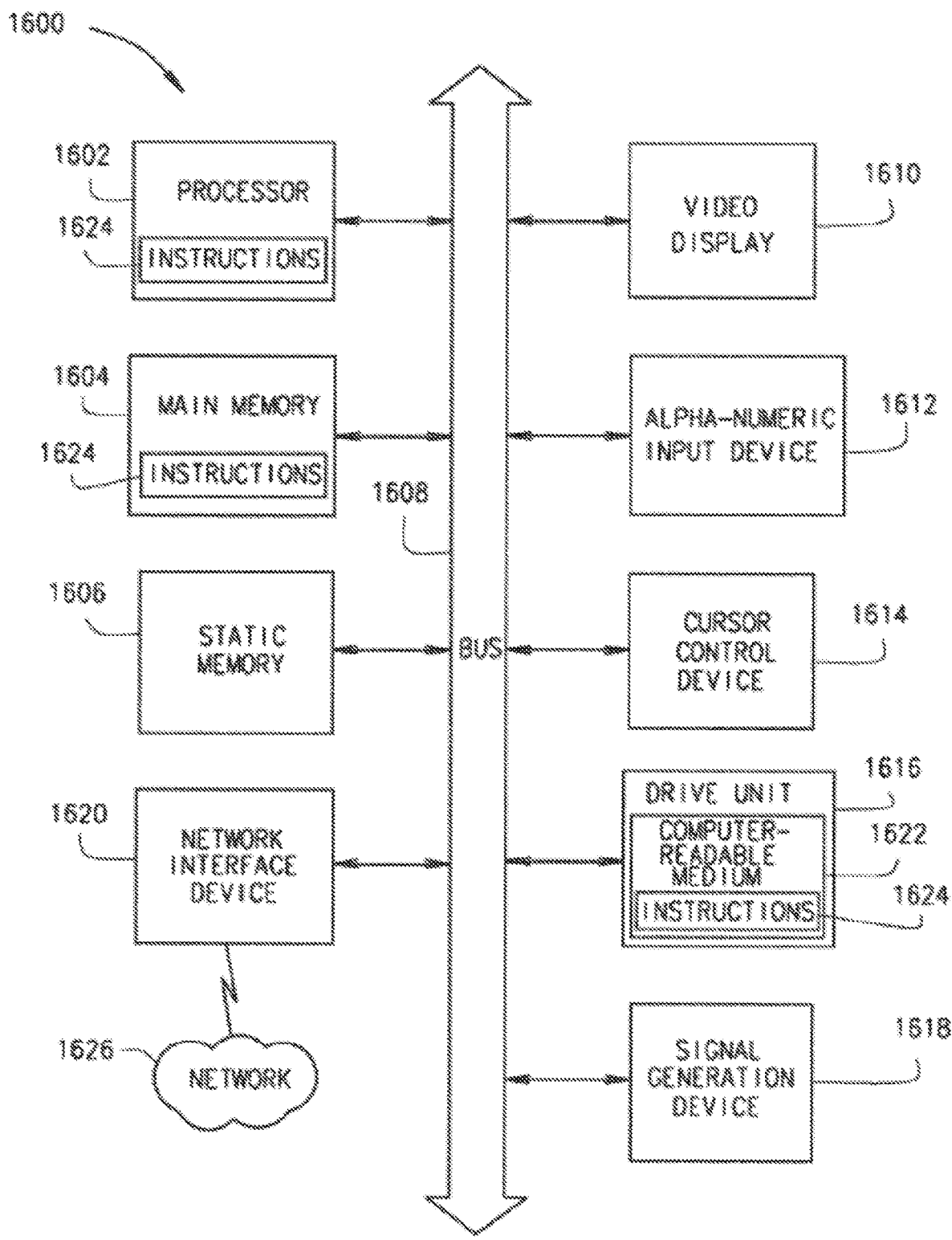
FIG. 10 shows a block diagram of a machine in the example form of a computer system within which a set of instructions may be executed causing the machine to perform any one or more of the methods, processes, operations, or methodologies discussed herein.

FIG. 10 shows a block diagram of a machine in the example form of a computer system 1600 within which a set of instructions may be executed causing the machine to perform any one or more of the methods, processes, operations, or methodologies discussed herein. The devices and/or system 800 described herein may include the functionality of the one or more computer systems 1600.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions sequential or otherwise) that specifies actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1600 includes a processor 1602 (e.g., a central processing unit (CPU) a graphics processing unit (GPU) or both), a main memory 1604 and a static memory 1606, which communicate with each other via a bus 1608. The computer system 1600 further includes a video display unit 1610 (e.g., a liquid crystal display (LCD) or a cathode ray tube (CRT)). The computer system 1600 also includes an alphanumeric input device 1612 (e.g., a keyboard), a cursor control device 1614 (e.g., a mouse), a drive unit 1616, a signal generation device 1618 (e.g., a speaker) and a network interface device 1620.

The drive unit 1616 includes a computer-readable medium 1622 on which is stored one or more sets of instructions (e.g., software 1624) embodying any one or more of the methodologies or functions described herein. The software 1624 may also reside, completely or at least partially, within the main memory 1604 and/or within the processor 1602 during execution thereof by the computer system 1600, the main memory 1604 and the processor 1602 also constituting computer-readable media.

The software 1624 may further be transmitted or received over a network 1626 via the network interface device 1620.

While the computer-readable medium 1622 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect other elements beyond those explicitly recited.

The inventive subject matter may be represented in a variety of different embodiments of which there are many possible permutations.

Thus, methods and systems for automated pharmaceutical dispensing have been described. Although embodiments of the present invention have been described with reference to specific example embodiments, it will be evident that various modifications and changes may be made to these embodiments without departing from the broader spirit and scope of the embodiments of the invention, Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion

What is claimed is:

1. A method for a pharmacy dispensing system, the method comprising:
    storing a plurality of drugs in multiple filling cabinets;
    prefilling the plurality of drugs from the multiple filling cabinets into a plurality of medication containers;
    automatically identifying at least one drug of the plurality of drugs to be dispensed from the plurality of medication containers into at least one consumer pill container;
    determining a distribution parameter for the containers, the distribution parameter representing one or more of a quantity of the drugs that is dispensed or a limit on dispensing the drugs;
    determining at least one drug allocation of the drugs in the medication containers that differs from a current allocation of the drugs in the medication containers; and
    changing the current allocation of the drugs in the medication containers to increase a distribution velocity at which the drugs are dispensed from the pharmacy dispensing system.

2. The method of claim 1, wherein the medication containers within the filling cabinets separately hold a different group of the drugs.

3. The method of claim 1, wherein the distribution parameter represents one or more of:
    a first number of units of the drugs are distributed per unit time,
    a filling frequency that the medication containers are filled with the drugs within a designated period of time,
    a second number of the medication containers are filled with the same drug,
    a third number of the medication containers in the same filling cabinet are filled with the same drug,
    a fourth number of the medication containers in different filling cabinets of the filling cabinets are filled with the same drug, or
    a depletion frequency that the medication containers are depleted of the corresponding drugs.

4. The method of claim 1, wherein the distribution parameter represents one or more of:
    a lower limit on a number of the different drugs that are required to be in the filling cabinets, or an upper limit on how many units of the drugs can be dispensed from the medication containers.

5. The method of claim 1, wherein the distribution parameter represents a co-morbidity relationship between the drugs.

6. The method of claim 1, wherein the distribution parameter represents several different co-morbidity relationships between the drugs that are associated with different geographic areas.

7. The method of claim 1, wherein the current allocation of the drugs in the medication containers is changed by increasing how many of the medication containers include the same drug.

8. A tangible and non-transitory computer readable medium comprising instructions that direct one or more processors to:
   automatically identify at least one drug of a plurality of drugs to be dispensed from a plurality of medication containers in multiple filling cabinets into at least one consumer pill container;
   determine a distribution parameter for the medication containers, the distribution parameter representing one or more of a quantity of the drugs that is dispensed or a limit on dispensing the drugs;
   determine at least one drug allocation of the drugs in the medication containers that differs from a current allocation of the drugs in the medication containers; and
   change the current allocation of the drugs in the medication containers to increase a distribution velocity at which the drugs are dispensed from the pharmacy dispensing system.

9. The tangible and non-transitory computer readable medium of claim 8, wherein the medication containers within the filling cabinets separately hold a different group of the drugs.

10. The tangible and non-transitory computer readable medium of claim 8, wherein the distribution parameter represents one or more of:
    a first number of units of the drugs are distributed per unit time,
    a filling frequency that the medication containers are filled with the drugs within a designated period of time,
    a second number of the medication containers are filled with the same drug, a third number of the medication containers in the same filling cabinet are filled with the same drug,
    a fourth number of the medication containers in different filling cabinets of the filling cabinets are filled with the same drug, or
    a depletion frequency that the medication containers are depleted of the corresponding drugs.

11. The tangible and non-transitory computer readable medium of claim 8, wherein the distribution parameter represents a lower limit on a number of the different drugs that are required to be in the filling cabinets.

12. The tangible and non-transitory computer readable medium of claim 8, wherein the distribution parameter represents an upper limit on how many units of the drugs can be dispensed from the medication containers.

13. The tangible and non-transitory computer readable medium of claim 8, wherein the distribution parameter represents a co-morbidity relationship between the drugs.

14. The tangible and non-transitory computer readable medium of claim 8, wherein the distribution parameter represents several different co-morbidity relationships between the drugs that are associated with different geographic areas.

15. A method comprising:
    identifying several drugs to be dispensed from medication containers within filling cabinets in a pharmacy dispensing system, the medication containers within the filling cabinets including separate vessels each holding a different group of the drugs, the drugs automatically dispensed from the drug containers into separate pill containers;
    determining a distribution parameter for the medication containers, the distribution parameter representing one or more of a quantity of the drugs that is dispensed or a limit on dispensing the drugs;
    determining at least one allocation of the drugs in the medication containers that differs from a current allocation of the drugs in the medication containers; and
    changing the current allocation of the drugs in the medication containers to increase a distribution velocity at which the drugs is dispensed from the pharmacy dispensing system, the current allocation changed such that a different number of the medication containers holds the same drug.

16. The method of claim 15, wherein the distribution parameter represents one or more of:
    a first number of units of the drugs is distributed per unit time,
    a filling frequency that the medication containers are filled with the drugs within a designated period of time,
    a second number of the medication containers are filled with the same drug, a third number of the medication containers in the same filling cabinet are filled with the same drug,
    a fourth number of the medication containers in different filling cabinets of the filling cabinets are filled with the same drug, or
    a depletion frequency that the medication containers are depleted of the drugs.

17. The method of claim 15, wherein the distribution parameter represents a lower limit on a number of the different drugs that are required to be in the filling cabinets.

18. The method of claim 15, wherein the distribution parameter represents an upper limit on how many units of the drugs can be dispensed from the medication containers.

19. The method of claim 15, wherein the distribution parameter represents a co-morbidity relationship between the drugs.

20. The method of claim 15, wherein the distribution parameter represents several different co-morbidity relationships between the drugs that are associated with different geographic areas.

* * * * *